United States Patent [19]

Maughan

[11] 4,446,131

[45] May 1, 1984

[54] CONTROLLED TEMPERATURE PROCESS FOR MANUFACTURING OF IMPROVED STABILIZED ALOE VERA

[75] Inventor: Rex G. Maughan, Tempe, Ariz.

[73] Assignee: Aloe Vera of America, Inc., Dallas, Tex.

[21] Appl. No.: 386,702

[22] Filed: Jun. 9, 1982

[51] Int. Cl.³ .................... A61K 35/78; C07G 17/00
[52] U.S. Cl. ................................ 424/195; 260/236.5
[58] Field of Search ...................... 260/236.5; 424/195

[56] References Cited

U.S. PATENT DOCUMENTS 4,178,372 12/1979 Coats .................................. 424/195

OTHER PUBLICATIONS

Merck Index 9th ed., p. 1290, Vitamin E, 1976.

Primary Examiner—Sam Rosen
Assistant Examiner—J. W. Rollins
Attorney, Agent, or Firm—Richards, Harris & Medlock

[57] ABSTRACT

A controlled temperature process for stabilizing aloe vera gel and the resulting gel which exhibits improved shelf life. The process including the steps of heating the aloe vera gel to a temperature in the range of from about 35° C. to about 70° C., admixing therewith stabilizing ingredients, cooling the admixed gel to ambient temperature in less than an hour.

8 Claims, No Drawings

CONTROLLED TEMPERATURE PROCESS FOR MANUFACTURING OF IMPROVED STABILIZED ALOE VERA

TECHNICAL FIELD

This invention relates to the processing of aloe vera gel, and more particularly to a controlled temperature process in which antioxidants and other stabilizing ingredients are used, resulting in significantly improved shelf life.

BACKGROUND ART

Aloe vera, a tropical or subtropical plant of the genus Aloe, has lance-shaped leaves with jagged edges and sharp points. The leaves contain a viscous but essentially clear gel given structural rigidity by hair-like connected fibers that run through it. Freshly excised from the plant and applied in vitro, this gel has been used medicinally for centuries by those living where the plant normally grows to relieve the pain of plant and animal stings, such as jelly fish stings.

The clear gel of aloe vera is to be distinguished from the thick, mucilaginous yellow juice that occurs about the base of the plant leaves and adjacent to the rind of the leaf. This juice, known as aloin, has been used for many years as an ingredient in many cathartics and purges.

The therapeutic qualities of the clear gel of the aloe vera depends on the freshness of the gel. For example, the pain of a jelly fish sting may be stopped, not to reoccur by applying the clear gel from a leaf that has just been cut, but if the gel has been exposed to air and light for about one and one-half hours, these powers are partially lost. Gel that has been removed from a freshly cut leaf for as little as three hours is only about 40% as effective as fresh gel. Yet, fever blisters have been treated successfully with gel that has been extracted for several weeks, though not with gel as old as three months. Apparently, the varying efficacy of the fresh gel for different medicinal purposes reflects the fact that the gel is a complex mixture of substances whose stability on exposure to air and light differ from one batch to another. In addition to loss of therapeutic efficacy on aging, decomposition products occur after a short time that may make the natural gel even less useful than it might be.

Several processes have been provided to prolong the effective life of the aloe vera extract. These attempts include U.S. Pat. No. 3,878,179 which discloses a process for the extraction and stabilization of the aloe vera gel by treating it under ultra violet radiation at ambient temperature to produce a biologically sterile and chemically stable extract. Other processes for stabilizing aloe vera gel are disclosed in U.S. Pat. Nos. 3,892,853 and 4,178,372.

U.S. Pat. No. 3,892,853 discloses a method to stabilize gel by adding catalytic portions of a nontoxic oxidant and heating the gel from 35° C. to about 80° C., the processed gel is then buffered to maintain a pH in the range of 4 to 8. Other ingredients may also be added to achieve desired or cosmetic purposes.

U.S. Pat. No. 4,178,372 discloses a process for stabilizing aloe vera gel utilizing a non-toxic oxidant, heating the gel from about 35° C. to about 80° C., after which ascorbic acid and a buffer is added to produce a hypoallergenic stabilized aloe vera gel.

The popularity of aloe vera products has dramatically increased, expanding the market area for the gels far beyond the regions where aloe vera may be grown. Thus, as the distance of the market area has increased from the area of production, a need has arisen to provide an aloe vera gel of improved stability. While earlier processes have increased the shelf life of the product, improvement has been needed. The present invention provides a method whereby the shelf life of aloe vera gel extract can be significantly increased.

SUMMARY OF THE INVENTION

The present invention is directed to a method of producing a stabilized aloe vera gel exhibiting improved stability. The improved aloe vera gel product is produced by mechanically separating the aloe vera gel matrix from the outer cortex of the aloe vera leaf and, after filtering particles of the aloe vera leaf from the gel matrix, the extracted gel is then mixed in a suitable vessel equipped for temperature control and heated to the range of from about 30° C. to about 70° C. When the gel reaches this range, ascorbic acid is added to compensate for the loss due to oxidation and exposure to air; while maintaining temperature and continuing mixing, other ingredients can be added to stabilize the color, stabilize the oxidant, and to adjust pH, as well as surfactants. The hot gel is admixed for a sufficient period of time so that it is thoroughly admixed and bacteria is killed. The hot gel is immediately passed to a heat exchanger where the temperature is dropped to ambient temperature or below (25° C. or below) within about one hour. The gel once cooled to ambient temperature is then ready for storage at room temperature and will exhibit an increased shelf life.

In the preferred embodiment, the aloe vera matrix is extracted from the plant in a vessel equipped for temperature control and heated in the range of from about 45° C. to about 70° C. When the gel attains a temperature within the range, ascorbic acid is added in an amount from about 0.05% to about 0.5% and one or more of the following standardizing ingredients and preferably all of them are added: citric acid in an amount ranging from about 0.01% to about 0.5%, sorbitol powder from about 1% to about 6%, sodium benzoate from about 0.05% to 0.5%, cetyl alcohol from 0.001% to 0.05% and a color stabilizer such as tocopherol or Vitamin E from 0.006% to about 0.01%. All percentages expressed herein are based upon the weight of the gel being processed. The aloe vera gel and combined ingredients are mixed thoroughly and preferably for at least 10 minutes. The gel is then rapidly cooled to ambient temperature (25° C. or below) in less than 1 hour. This method produces a gel with good color and composition which is almost identical to fresh gel and which does not oxidize easily and has a significantly increased shelf life.

DETAILED DESCRIPTION

The raw material for preparing the improved stabilized aloe vera gel of the present invention is obtained from the leaves of fully mature aloe vera plants. Maturity is measured by all active ingredients being present in the leaf in full concentration. A two year old plant is usually not mature; therefore, plants which are four to five years old are preferred to assure full maturity and because they have broader leaves, are easier to handle and contain larger amounts of gel, a factor that lowers percent gel losses when gel is separated from the leaf.

It is preferable that the leaves be processed immediately after cutting, because degradative decomposition of the gel begins upon cutting due to enzymatic reactions and the activity of bacteria normally present in the leaves. After the leaves are cut, they are carefully washed with clean water and are preferably soaked for about five minutes in a suitable nonirritative bacteriacide and fungicide, such as Microthene. The gel is then separated from the leaf by cutting off each end of the leaf and passing it under a roller to extrude the gel. The extruded gel is then collected and large foreign particles such as the cortex of the leaf are separated. Large foreign particles may be extracted by passing the gel through a series of apertures sized to retain the above type of particles. Extruders which are commercially available and designed for orange juice processing (for the purpose of removing pulp from the juice) can be used with good results. Those skilled in the art will recognize other methods of separating the gel from the leaf and separating large foreign particles from the gel may be employed. The aloe vera gel is then transferred to a mixing vessel equipped for temperature control and contains an agitator to impart shear to the gel. Preferably the mixing vessel and equipment are made of stainless steel to minimize contamination of the product. Shear may be imparted to the gel by any suitable means such as a stainless steel shearing pump or by a bladed agitator. A suitable mixing vessel can be constructed of stainless steel and equipped with a heating or cooling jacket.

After the gel has been introduced into the mixing vessel, it is agitated and heated to a temperature in the range of from about 35° C. to about 70° C. and preferably to about 49° C. Once the gel is within this range, ascorbic acid is added in an amount sufficient to compensate for the loss due to oxidation and exposure of the natural gel to the air. It has been found that the addition of absorbic acid in an amount from 0.05% to about 0.5% is sufficient. Preferably, the gel is heated to a temperature and for a period of time sufficient to kill bacteria which may be present. The gel is preferably heated for more than ten minutes and most preferably at 49° C. for about ten minutes. In addition to ascorbic acid, the potassium salt of ascorbic acid may also be utilized.

While holding the temperature at the predetermined temperature and while maintaining the temperature at the predetermined temperature with continued agitation, standardizing ingredients may be added which include the following: citric acid in an amount from 0.01% to about 0.5%, sorbitol powder from 1% to about 6%, sodium benzoate from 0.05% to about 0.5%, cetyl alcohol from 0.001% to 0.05% and tocopherol. Preferably, all of the standardizing ingredients are added. While maintaining temperature, the mixture is admixed for at least 10 minutes to assure intimate admixture of the product.

The gel is then rapidly cooled either in a heat exchanger or in the mixing vessel. Preferably, cooling is done in a second heat exchange vessel in order that the mixing vessel may be used for subsequent batches. The hot mix gel is cooled at a rate sufficient to lower its temperature to ambient temperature (about 25° C.) or lower in less than one hour. The cooled gel may then be packaged and stored at ambient temperature, and will exhibit a substantially improved shelf life over gel products produced by other methods.

The cetyl alcohol functions as a non-toxic surface active agent. Other surface active agents such as Tween 80, a polyoxyethlene (20) sorbitan monooleate, sold by Atlas Chemical. Sorbitol powder is added to the mixture as a moisturizer and mold inhibitor. Sodium benzoate is added to the gel and functions as an antibacterial agent useful in preserving the fresh character of the gel.

Tocopherols are added to stabilize the color of the gel. Changes in color of the stabilized gel may occur and although these color changes do not affect the therapeutic efficacy of stabilized preparations, they are undesirable because psychologically a change in color during storage suggests spoilage. Accordingly, a sufficient quantity of tocopherols to inhibit such a color change can be added. Vitamin E is one such tocopherol; and mixtures of alpha, beta, gamma and delta tocopherols can be employed.

While this invention has been described in relation to its preferred embodiments, it is to be understood that various modifications thereof will now be apparent to one skilled in the art upon reading the specification and it is intended to cover all such modifications as fall within the scope of the appended claims.

I claim:

1. A process for stabilizing a clear gel which has been separated from the leaf of aloe vera comprising:
   (a) heating said aloe vera gel to a temperature in the range of from about 35° C. to about 70° C.;
   (b) adding to said heated aloe vera gel ascorbic acid in an amount from about 0.05% to 0.5% based on the weight of said gel;
   (c) maintaining the admixed aloe vera gel and ascorbic acid at a temperature in the range of from about 35° C. to about 70° C. for a sufficient period of time to kill bacteria; and
   (d) cooling the aloe vera gel to ambient temperature or lower in less than one hour.

2. The process of claim 1 wherein the gel in step (a) is heated for more than 10 minutes.

3. A process for stabilizing a clear gel which has been separated from the leaf of aloe vera comprising:
   (a) heating said aloe vera gel to a temperature in the range of from about 35° C. to about 70° C.;
   (b) admixing with the heated gel the following:

| Ingredient | % Based On Weight Of Gel |
| --- | --- |
| (i) citric acid | 0.01 to about 0.5 |
| (ii) sorbitol powder | 1.0 to about 6.0 |
| (iii) sodium benzoate | 0.05 to about 0.5 |
| (iv) cetyl alcohol | 0.001 to about 0.05 |
| (v) tocopherol | 0.006 to about 0.01 |
| (vi) ascorbic acid | 0.05% to about 0.5% |

(c) heating said gel for a period of time sufficient to kill said bacteria; and
   (d) cooling the heated and admixed gel to ambient temperature or lower in less than one hour.

4. The process of claim 3 wherein said heated and admixed gel is heated to about 49° C. for about 10 minutes.

5. The process of claim 3 wherein said tocopherol is selected from the group consisting of Vitamin E, alpha tocopherol, beta tocopherol, gamma tocopherol, delta tocopherol and mixtures thereof.

6. The product produced by the process of claim 1.

7. The product produced by the process of claim 3.

8. The product produced by the process of claim 4.

* * * * *

UNITED STATES PATENT AND TRADEMARK OFFICE
CERTIFICATE OF CORRECTION

PATENT NO. : 4,446,131
DATED : May 1, 1984
INVENTOR(S) : Rex G. Maughan

It is certified that error appears in the above-identified patent and that said Letters Patent is hereby corrected as shown below:

Column 3, line 38, change "absorbic" to --ascorbic--.

Signed and Sealed this

Sixth Day of November 1984

[SEAL]

Attest:

GERALD J. MOSSINGHOFF

Attesting Officer

Commissioner of Patents and Trademarks